(12) United States Patent
Martin et al.

(10) Patent No.: US 10,874,771 B2
(45) Date of Patent: *Dec. 29, 2020

(54) ORIENTED P4HB IMPLANTS CONTAINING ANTIMICROBIAL AGENTS

(71) Applicant: Tepha, Inc., Lexington, MA (US)

(72) Inventors: David P. Martin, Lexington, MA (US); Said Rizk, Lexington, MA (US); Simon F. Williams, Lexington, MA (US); Arikha Moses, Lexington, MA (US)

(73) Assignee: TEPHA, INC., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/733,072

(22) Filed: Jan. 2, 2020

(65) Prior Publication Data

US 2020/0139018 A1 May 7, 2020

Related U.S. Application Data

(63) Continuation of application No. 14/860,857, filed on Sep. 22, 2015, now Pat. No. 10,525,172.

(60) Provisional application No. 62/053,451, filed on Sep. 22, 2014.

(51) Int. Cl.
| | |
|---|---|
| *A61L 31/06* | (2006.01) |
| *A61L 31/08* | (2006.01) |
| *A61L 31/16* | (2006.01) |
| *A61L 27/18* | (2006.01) |

(52) U.S. Cl.
CPC ........... *A61L 31/06* (2013.01); *A61L 27/18* (2013.01); *A61L 31/08* (2013.01); *A61L 31/16* (2013.01); *A61L 2300/404* (2013.01); *A61L 2420/02* (2013.01); *A61L 2420/06* (2013.01)

(58) Field of Classification Search
CPC .......... A61L 31/06; A61L 31/08; A61L 31/16; A61L 2420/02; A61L 2420/06; A61L 27/18; A61L 2300/404
See application file for complete search history.

(56) References Cited

U.S. PATENT DOCUMENTS

| | | | |
|---|---|---|---|
| 5,811,272 A | 9/1998 | Snell | |
| 5,853,745 A | 12/1998 | Darouiche | |
| 6,316,262 B1 | 11/2001 | Huisman | |
| 6,323,010 B1 | 11/2001 | Skraly | |
| 6,548,569 B1 | 4/2003 | Williams | |
| 6,555,123 B2 | 4/2003 | Williams | |
| 6,585,994 B2 | 7/2003 | Williams | |
| 6,610,764 B1 | 8/2003 | Martin | |
| 6,828,357 B1 | 12/2004 | Martin | |
| 6,838,493 B2 | 1/2005 | Williams | |
| 6,867,247 B2 | 3/2005 | Williams | |
| 6,867,248 B1 | 3/2005 | Martin | |
| 6,878,758 B2 | 4/2005 | Signer | |
| 7,025,980 B1 | 4/2006 | Williams | |
| 7,179,883 B2 | 2/2007 | Williams | |
| 7,268,205 B2 | 9/2007 | Williams | |
| 7,553,923 B2 | 6/2009 | Williams | |
| 7,618,448 B2 | 11/2009 | Schmitz | |
| 7,641,825 B2 | 1/2010 | Rizk | |
| 7,943,683 B2 | 5/2011 | Rizk | |
| 8,016,883 B2 | 9/2011 | Coleman | |
| 8,034,270 B2 | 10/2011 | Martin | |
| 8,039,237 B2 | 10/2011 | Martin | |
| 8,287,909 B2 | 10/2012 | Martin | |
| 8,747,468 B2 | 6/2014 | Martin | |
| 10,525,172 B2 * | 1/2020 | Martin | ............ A61L 27/18 |
| 2004/0253185 A1 | 12/2004 | Herweck | |
| 2005/0025809 A1 | 2/2005 | Hasirci | |
| 2009/0324738 A1 | 12/2009 | Krongauz | |

(Continued)

FOREIGN PATENT DOCUMENTS

| | | |
|---|---|---|
| WO | 1999032536 | 7/1999 |
| WO | 00056376 | 9/2000 |

(Continued)

OTHER PUBLICATIONS

Sadava et al., Does Presoaking Synthetic Mesh in Antibiotic Solution Reduce Mesh Infections? An Experimental Study, 2013, J. Gastrointest Surg, vol. 17, pp. 562-568. (Year: 2013).*
Martin et al., Medical Applications of Poly-4-hydroxybutyrate: a Strong Flexible Absorbable Biomaterial, 2003, vol. 16, pp. 97-105. (Year: 2003).*
Falagas and Kasiakou, Mesh-related infections after hernia repair surgery, Clin. Microbial. Infec., 11:3-8 (2005).
Hori, et al., "Chemical synthesis of high molecular weight poly(3-hydroxybutyrate-co-4-hydroxybutyrate)", Polymer 36:4703-5 (1995).
Houk, et al., "Why delta-valerolactone polymerizes and gamma-butyrolactone does not", J. Org. Chem., 73 (7), 2674-8 (2008).
International Search Report for corresponding PCT application PCT/US2015/051338 dated Nov. 13, 2015.
Martin, et al., "Characterization of poly-4-hydroxybutyrate mesdh for hernia repair applications", J Surg Res., 184:766-73 (2013).

(Continued)

*Primary Examiner* — Ali Soroush
(74) *Attorney, Agent, or Firm* — Pabst Patent Group LLP

(57) ABSTRACT

Oriented resorbable implants made from poly-4-hydroxybutyrate (P4HB) and copolymers thereof, have been developed that contain one or more antimicrobial agents to prevent colonization of the implants, and reduce or prevent the occurrence of infection following implantation in a patient. These oriented implants are particularly suitable for use in procedures where prolonged strength retention is necessary and there is a risk of infection. Coverings and receptacles made from poly-4-hydroxybutyrate and copolymers thereof, containing antimicrobial agents, have also been developed for use with implantable devices to prevent colonization of these devices, and to reduce or prevent the occurrence of infection following implantation of these devices in a patient. These coverings and receptacles may be used to hold, or partially or fully cover, devices such as pacemakers and neurostimulators. Preferably, the coverings and receptacles are made from meshes, non-wovens, films, fibers, and foams, and contain rifampin and minocycline.

16 Claims, No Drawings

(56) References Cited

U.S. PATENT DOCUMENTS

| | | |
|---|---|---|
| 2012/0022321 A1 | 1/2012 | Dinh |
| 2012/0053689 A1 | 3/2012 | Martin |
| 2012/0150285 A1 | 6/2012 | Cahil |
| 2012/0283826 A1 | 11/2012 | Moses |
| 2013/0090449 A1 | 4/2013 | Whitehouse |
| 2013/0309166 A1 | 11/2013 | Rizk |
| 2013/0309275 A1 | 11/2013 | Carter |
| 2014/0200667 A1 | 7/2014 | Carter |

FOREIGN PATENT DOCUMENTS

| | | | |
|---|---|---|---|
| WO | 200056376 | 9/2000 | |
| WO | WO-0056376 A1 * | 9/2000 | ............ A61L 31/16 |
| WO | 2004101002 | 11/2004 | |
| WO | WO-2004101002 A2 * | 11/2004 | ............ C08L 67/04 |
| WO | 2007092417 | 8/2007 | |
| WO | 2011119742 | 9/2011 | |
| WO | 2012064526 | 5/2012 | |
| WO | 2014070792 | 5/2014 | |
| WO | 2014137454 | 9/2014 | |

OTHER PUBLICATIONS

Martin, et al., "Medical Applications of Poly-4-hydroxybutyrate: A Strong Flexible Absorbable Biomaterial", Biochem. Eng. J. 16:97-105 (2003).

Moore, et al., "Chemosynthesis of bioresorbable poly(gamma-butyrolactone) by ring-opening polymerization: a review", Biomaterials, 26:3771-82 (2005).

Odermatt, et al., "MonoMax Suture: A New Long-TermAbsorbableMonofilamentSutureMade from Poly-4-Hydroxybutyrate", J Polymer Sci., Article 216137 (2012).

Pittet, Infection in breast implants, Lancet Infect Dis. 5:94-106 (2005).

Williams, et al., "Applications of PHAs in Medicine and Pharmacy, in Biopolymers", Polyesters, III, 4:91-127 (2002).

Williams, et al., "Poly-4-hydroxybutyrate (P4HB): a new generation of resorbable medical devices for tissue repair and regeneration", Biomed. Tech. 58(5):439-452 (2013).

Sadava, et al., "Does Presoaking Synthetic Mesh in Antibiotic Solution Reduce Mesh Infection? An Experimental Study", J. Gastrointest. Surg., 17:562-568 (2012).

* cited by examiner

US 10,874,771 B2

ORIENTED P4HB IMPLANTS CONTAINING ANTIMICROBIAL AGENTS

CROSS-REFERENCE TO RELATED APPLICATIONS

This application is a continuation of U.S. application Ser. No. 14/860,857, filed Sep. 22, 2015, which claims benefit of and priority to U.S. Provisional Application No. 62/053,451, filed Sep. 22, 2014, the contents of which are incorporated by reference herein in their entirety.

FIELD OF THE INVENTION

The present invention generally relates to oriented resorbable polymeric compositions that can be processed into implants or coverings and receptacles for implants. The implants contain antimicrobial or other anti-infectious agents, and are oriented. The polymeric compositions include resorbable poly-4-hydroxybutyrate (P4HB) and copolymers thereof.

BACKGROUND OF THE INVENTION

Nosocomial (hospital-acquired) infections are the most common infection in the hospital setting with an estimated 2 million infections in the US each year resulting in about 90,000 deaths per year. Implant-related infections continue to be a major problem in surgery, and their occurrence is still significant despite measures in hospitals to limit patient infection in the operating room. For example, (i) mesh-related infections following hernia repair procedures have been reported to be as high as 8% after open incisional hernia repair with mesh (Falagas and Kasiakou, Mesh-related infections after hernia repair surgery, *Clin. Microbiol. Infec.* 11:3-8 (2005), (ii) rates of infection after breast implantation have been reported to range from 2.0-2.5% (Pittet, Infection in breast implants, *Lancet Infect Dis.* 5:94-106 (2005), (iii) the incidence of infections after hip and knee replacements in the US has been reported to be between 0.67% and 2.4%, and (iv) the incidence of infection in patients implanted with pacemakers is reported to have increased by 224% from 1.6% in 1993 to 3.5% in 2008.

In addition to efforts to reduce patient contamination both in the operating room and on the way to the operating room, medical device manufacturers have introduced various implants that contain antimicrobial agents to reduce or inhibit microbial colonization on a medical device, and to reduce or prevent device-related infections. For example, the Codman BACTISEAL® Catheter and Medtronic ARES® Catheter both contain clindamycin and rifampin to reduce infection when these devices are implanted to drain cerebrospinal fluid; Smith & Nephew's ORTHOGUARD® product contains gentamicin to prevent infection around orthopedic wires and pins; Gore's DUAL MESH® contains silver carbonate and chlorhexidine acetate to prevent infection after hernia and soft tissue repair; and Depuy's PROSTALAC® hip system contains tobramycin and vancomycin to prevent infection following total hip replacement.

Recently, a number of implantable devices made from, or containing, poly-4-hydroxybutyrate (P4HB), a resorbable thermoplastic polymer, have been introduced. For example, hernia repair products made from P4HB fibers have been disclosed by Martin et al. Characterization of poly-4-hydroxybutyrate mesh for hernia repair applications, *J. Surg. Res.* 184:766-773 (2013), and sutures made from P4HB monofilament have been disclosed by Odermatt et al. A new long-term absorbable monofilament suture made from poly-4-hydroxybutyrate, *Journal of Polymer Science*, 2012 Article 216137, 12 pages. Other P4HB medical devices have been disclosed by Williams et al. Poly-4-hydroxybutyrate (P4HB): a new generation of resorbable medical devices for tissue repair and regeneration. *Biomed Tech* (Berl), 2013, ISSN (Online) 1862-278X, ISSN (Print) 0013-5585, DOI: 10.1515/bmt-2013-0009. However, none of these P4HB devices contain antimicrobial agents to prevent colonization of the device and/or to reduce or prevent infection.

There is thus a need to develop implants of P4HB and copolymers thereof that contain and release one or more antimicrobial agents to prevent colonization of the implants and/or to reduce or prevent infection.

It is an object of the present invention to provide oriented implants of P4HB and copolymers thereof that contain one or more antimicrobial agents to prevent colonization of the implants and/or to reduce or prevent infection following implantation in a patient.

It is a further object of the present invention to provide processes to produce oriented implants of P4HB and copolymers thereof that contain antimicrobial agents suitable for the prevention of implant colonization and/or to reduce or prevent infection.

It is still another object of the invention to provide methods for implantation of oriented implants made from P4HB and copolymers thereof that contain antimicrobial agents.

SUMMARY OF THE INVENTION

Oriented resorbable implants made from poly-4-hydroxybutyrate (P4HB) and copolymers thereof, have been developed that contain one or more anti-microbial agents to prevent colonization of the implants, and reduce or prevent the occurrence of infection following implantation in a patient. These oriented implants are particularly suitable for use in procedures where prolonged strength retention is necessary and where there is a risk of infection, such as hernia repair, breast reconstruction and augmentation, mastopexy, orthopedic repairs, wound management, pelvic floor reconstruction, stenting, heart valve surgeries, dental procedures and other plastic surgeries.

In a preferred embodiment, the oriented implants are made from fibers and meshes comprising poly-4-hydroxybutyrate coated with rifampin and minocycline. Coverings and receptacles made from oriented forms of poly-4-hydroxybutyrate and copolymers thereof, containing antimicrobial agents, have also been developed for use with cardiac rhythm management devices and other implantable devices to prevent colonization of these devices, and to reduce or prevent the occurrence of infection following implantation of these devices in a patient. These coverings and receptacles may be used to hold, or partially or fully cover, devices such as pacemakers and neurostimulators. In a preferred embodiment, the coverings and receptacles are made from meshes, non-wovens, films, fibers, and foams, and contain rifampin and minocycline.

In other embodiments, the devices formed of oriented P4HB and copolymers thereof that contain and release one or more antimicrobial agents to prevent colonization of the implants and/or to reduce or prevent infection are a suture, barbed suture, braided suture, monofilament suture, hybrid suture of monofilament and multifilament fibers, braids, ligatures, knitted or woven meshes, knitted tubes, catheters, monofilament meshes, multifilament meshes, patches, wound healing device, bandage, wound dressing, burn dressing, ulcer dressing, skin substitute, hemostat, tracheal reconstruction device, organ salvage device, dural substitute, dural patch, nerve guide, nerve regeneration or repair device, hernia repair device, hernia mesh, hernia plug, device for temporary wound or tissue support, tissue engineering scaffold, guided tissue repair/regeneration device, anti-adhesion membrane, adhesion barrier, tissue separation membrane, retention membrane, sling, device for pelvic floor reconstruction, urethral suspension device, device for treatment of urinary incontinence, device for treatment of vesicoureteral reflux, bladder repair device, or sphincter muscle repair device. Other embodiments include injectable particles including microspheres, bulking or filling device, bone marrow scaffold, clip, clamp, screw, pin, nail, medullary cavity nail, bone plate, interference screw, tack, fastener, rivet, staple, fixation device for an implant, bone graft substitute, bone void filler, suture anchor, bone anchor, ligament repair device, ligament augmentation device, ligament graft, anterior cruciate ligament repair device, tendon repair device, tendon graft, tendon augmentation device, rotator cuff repair device, meniscus repair device, meniscus regeneration device, articular cartilage repair device, osteochondral repair device, spinal fusion device, viscosupplement, or other device for treatment of osteoarthritis. In still other embodiments, the devices are a stent, including coronary, cardiovascular, peripheral, ureteric, urethral, urology, gastroenterology, nasal, ocular, or neurology stents and stent coatings, stent graft, cardiovascular patch, catheter balloon, vascular closure device, intracardiac septal defect repair device, including atrial septal defect repair devices and PFO (patent foramen ovale) closure devices, left atrial appendage (LAA) closure device, pericardial patch, vein valve, heart valve, heart valve ring, vascular graft, or myocardial regeneration device. Other embodiments include periodontal mesh, guided tissue regeneration membrane for periodontal tissue, ocular cell implant, imaging device, cochlear implant, embolization device, anastomosis device, plastic surgery device, breast lift device, mastopexy device, breast reconstruction device, breast augmentation device (including devices for use with breast implants), breast reduction device (including devices for removal, reshaping and reorienting breast tissue), devices for breast reconstruction following mastectomy with or without breast implants, facial reconstructive device, forehead lift device, brow lift device, eyelid lift device, face lift device, rhytidectomy device, thread lift device (to lift and support sagging areas of the face, brow and neck), rhinoplasty device, device for malar augmentation, otoplasty device, neck lift device, mentoplasty device, cosmetic repair device, and device for facial scar revision. Additional embodiments include enclosures, pouches, holders, covers, meshes, non-wovens, films, clamshells, casings, and other receptacles made from oriented P4HB and copolymers thereof that partially or fully encase, surround or hold implantable medical devices, and wherein the oriented P4HB and copolymers thereof contain and release one or more antimicrobial agents to prevent colonization of the implants and/or reduce or prevent infection, for example by partially or fully encasing, surrounding or holding cardiac rhythm management (CRM) devices, including pacemakers, defibrillators and generators, implantable access systems, neurostimulators, ventricular access devices, infusion pumps, devices for delivery of medication and hydration solutions, intrathecal delivery systems, pain pumps, and other devices to provide drugs or electrical stimulation to a body part.

DETAILED DESCRIPTION OF THE INVENTION

Methods have been developed to prepare oriented resorbable implants that contain one or more antimicrobial agents to prevent colonization of the implants, and reduce or prevent the occurrence of infection following implantation in a patient. After implantation, the implants are designed to release the antimicrobial agents. The resorbable implants are preferably made from P4HB and copolymers thereof. In one embodiment, the implant releases antimicrobial agent for at least 2-3 days. The implants are particularly suitable for use in procedures where there is a risk of infection, such as hernia repair, breast reconstruction and augmentation, mastopexy, orthopedic repairs, wound management, pelvic floor reconstruction, stenting, heart valve surgeries, dental procedures and other plastic surgeries. In a preferred embodiment, methods have been developed to produce highly oriented fibers and meshes of P4HB and copolymers thereof that contain the antimicrobial agents. Maintenance of the high degree of orientation of these fibers and meshes is essential to their physical function in vivo. The high degree of orientation of the fibers and meshes allows these devices to retain strength in the body for prolonged periods ("prolonged strength retention"), and therefore provide critical support to tissues during reconstruction and repair procedures. If orientation is lost during preparation of the antimicrobial-containing fibers and meshes, the resulting products will have lower strength and strength retention, and be unable to provide the necessary reinforcement and configuration required for healing. For example, spray coating or dip coating of oriented P4HB fibers using many solvents results in loss of fiber orientation and loss of strength retention. Methods have been developed that allow fibers and meshes of P4HB and copolymers thereof containing antimicrobials to be prepared without substantial loss of orientation of the fibers, and therefore without substantial loss of strength and strength retention.

Methods have also been developed to prepare resorbable enclosures, pouches, holders, covers, meshes, non-wovens, films, clamshells, casings, and other receptacles made from P4HB and copolymers thereof that partially or fully encase, surround or hold implantable medical devices, and wherein the P4HB and copolymers thereof contain and release one or more antimicrobial agents to prevent colonization of the implants and/or reduce or prevent infection. Implantable medical devices that can be partially or fully encased include cardiac rhythm management (CRM) devices (including pacemakers, defibrillators, and generators), implantable access systems, neurostimulators, ventricular access devices, infusion pumps, devices for delivery of medication and hydration solutions, intrathecal delivery systems, pain pumps, and other devices to provide drugs or electrical stimulation to a body part.

In one embodiment, the methods disclosed herein are based upon the discovery that certain solvents and solvent mixtures can be used to apply antimicrobial agents to oriented constructs of P4HB and copolymers thereof, such as fibers and meshes, without causing de-orientation of the constructs. The solvents and solvent mixtures are essentially non-solvents or poor solvents for oriented constructs of P4HB and copolymers thereof, but can dissolve the antimicrobial agents. Furthermore, upon application to the constructs of P4HB and copolymers thereof, the solvents either evaporate, can be removed by washing with another non-solvent for the construct, or can be readily dried, and leave behind the antimicrobial agents on the constructs. Suitable solvents for applying antimicrobial agents to oriented constructs of P4HB and copolymers thereof, must therefore be (i) non-solvents or poor solvents for the constructs, (ii) capable of dissolving the antimicrobial agents in suitable concentrations, (iii) volatile or easily removed from the construct using, for example, low heat or another non-solvent for the construct, and (iv) non-reactive and non-toxic.

I. Definitions

"Bioactive agent" is used herein to refer to therapeutic, prophylactic or diagnostic agents, preferably agents that promote healing and the regeneration of host tissue, and also therapeutic agents that prevent, inhibit or eliminate infection agent" includes a single such agent and is also intended to include a plurality.

"Bicomponent" as generally used herein means a structure containing two or more materials.

"Blend" as generally used herein means a physical combination of different polymers, as opposed to a copolymer formed of two or more different monomers.

"Burst pressure" as used herein is determined according to ASTM D6797-02 (Standard Test Method for Bursting Strength of Fabrics Constant-Rate-of-Extension (CRE) Ball Burst Test) at ambient conditions using a ball burst fixture with a 1.6 cm circular opening and a 1 cm diameter half-rounded probe.

"Copolymers of poly-4-hydroxybutyrate" as generally used herein means any polymer containing 4-hydroxybutyrate with one or more different hydroxy acid units.

"Molecular weight" as used herein, unless otherwise specified, refers to the weight average molecular weight (Mw), not the number average molecular weight (Mn), and is measured by GPC relative to polystyrene.

"Poly-4-hydroxybutyrate" as generally used herein means a homopolymer containing 4-hydroxybutyrate units. It can be referred to herein as P4HB or TephaFLEX® biomaterial (manufactured by Tepha, Inc., Lexington, Mass.).

"Elongation" or "extensibility" of a material means the amount of increase in length resulting from, as an example, the tension to break a specimen. It is expressed usually as a percentage of the original length. (Rosato's Plastics Encyclopedia and Dictionary, Oxford Univ. Press, 1993).

"Molecular weight" as used herein, unless otherwise specified, refers to the weight average molecular weight (Mw), not number average molecular weight (Mn), and is measured by gel permeation chromatography (GPC) relative to polystyrene.

"Resorbable" as generally used herein means the material is broken down in the body and eventually eliminated from the body. The terms "resorbable", "degradable", "erodible", and "absorbable" are used somewhat interchangeably in the literature in the field, with or without the prefix "bio". Herein, these terms will be used interchangeably to describe material broken down and gradually absorbed or eliminated by the body within five years, whether degradation is due mainly to hydrolysis or mediated by metabolic processes.

"Strength retention" refers to the amount of time that a material maintains a particular mechanical property following implantation into a human or animal. For example, if the tensile strength of a resorbable fiber decreased by half over 3 months when implanted into an animal, the fiber's strength retention at 3 months would be 50%.

"Suture pullout strength" as used herein means the peak load (kg) at which an implant fails to retain a suture. It is determined using a tensile testing machine by securing an implant in a horizontal holding plate, threading a suture in a loop through the implant at a distance of 1 cm from the edge of the implant, and securing the suture arms in a fiber grip positioned above the implant. Testing is performed at a crosshead rate of 100 mm/min, and the peak load (kg) is recorded. The suture is selected so that the implant will fail before the suture fails.

"Taber Stiffness Unit" is defined as the bending moment of ⅕ of a gram applied to a 1½" (3.81 cm) wide specimen at a 5 centimeter test length, flexing it to an angle of 15°, and is measured using a Taber V-5 Stiffness Tester Model 150-B or 150-E. The TABER® V-5 Stiffness Tester—Model 150-B or 150-E is used to evaluate stiffness and resiliency properties of materials up to 10,000 Taber Stiffness Units. This precision instrument provides accurate test measurement to ±1.0% for specimens 0.004" to 0.219" thickness. One Taber Stiffness Unit is equal to 1 gram cm (g cm) or 0.0981 milliNewton meters (mN m). Taber Stiffness Units can be converted to Genuine Gurley™ Stiffness Units with the equation: $S_T=0.01419S_G-0.935$, where $S_T$ is the stiffness in Taber Stiffness Units and $S_G$ is the stiffness in Gurley Stiffness Units. To convert Taber Stiffness Units to Millinewton Meters, use the equation: $X=S_T*0.098067$, where X is the stiffness in Millinewton Meters.

"Tensile modulus" is the ratio of stress to strain for a given material within its proportional limit.

II. Compositions

Methods have been developed to (i) produce oriented resorbable implants comprising P4HB and copolymers thereof that contain one or more antimicrobial agents to prevent colonization of the implants, and reduce or prevent the occurrence of infection following implantation in a patient, and (ii) produce resorbable enclosures, pouches, holders, covers, meshes, non-wovens, films, clamshells, casings, and other receptacles made from P4HB and copolymers thereof that partially or fully encase, surround or hold implantable medical devices, and the devices, wherein the P4HB and copolymers thereof contain and release one or more antimicrobial agents to prevent colonization of the implants and/or reduce or prevent infection.

A. P4HB and Copolymers

The methods described herein can typically be used to produce resorbable implants and resorbable enclosures, pouches, holders, covers, meshes, non-wovens, films, clamshells, casings, and other receptacles from P4HB and copolymers thereof. Copolymers include 4-hydroxybutyrate with 3-hydroxybutyrate, and 4-hydroxybutyrate with glycolic acid monomer. P4HB and copolymers thereof can be obtained from Tepha, Inc. of Lexington, Mass. Preferred polymers and copolymers have a weight average molecular weight (Mw) of 50,000 to 1,200,000, and more preferably 100,000 to 800,000 based on gel permeation chromatography (GPC) relative to polystyrene standards.

Poly-4-hydroxybutyrate (P4HB) is not a natural product, but P4HB and copolymers thereof can be produced using transgenic fermentation methods, see, for example, U.S. Pat. No. 6,548,569 to Williams et al. Poly-4-hydroxybutyrate (P4HB, TephaFLEX® biomaterial) is a strong, pliable thermoplastic polyester that, despite its biosynthetic route, has a relatively simple structure, and belongs to a class of polymers known as polyhydroxyalkanoates (PHAs). The physical properties of unoriented P4HB are shown in Table 1. Chemical synthesis of P4HB has been attempted, but it has been impossible to produce the polymer with a sufficiently high molecular weight that is necessary for most applications, including melt processing (see Hori, Y., et al., *Polymer* 36:4703-4705 (1995); Houk, K. N., et al., *J. Org. Chem.*, 2008, 73 (7), 2674-2678; and Moore, T., et al., *Biomaterials* 26:3771-3782 (2005)). In fact, it has been calculated to be thermodynamically impossible to chemically synthesize a high molecular weight P4HB homopolymer under normal conditions (Moore, T., et al., *Biomaterials* 26:3771-3782 (2005)). Chemical synthesis of P4HB instead yields short chain oily oligomers that lack the desirable thermoplastic properties of the high molecular weight P4HB polymers produced by biosynthetic recombinant methods.

TABLE 1

Physical & thermal properties of un-oriented P4HB homopolymer

| Property | |
|---|---|
| Tensile Strength (MPa) | 50 |
| Tensile Modulus (MPa) | 70 |
| Elongation at break (%) | ~1,000 |
| Tm (° C.) | 60 |
| Tg (° C.) | −51 |

The literature commonly refers to another polyhydroxyalkanoate, poly-3-hydroxybutyrate (P3HB), simply as polyhydroxybutyrate (PHB) (see Section 2 of Moore, T., et al., *Biomaterials* 26:3771-3782 (2005)). PHB (or P3HB) has entirely different properties to P4HB. It is structurally and functionally different to P4HB. For example, PHB has a melting point of 180° C. versus a melting point of about 61° C. for P4HB. The polymers also have substantially different glass transition temperatures and mechanical properties. For example, PHB is a relatively hard brittle polymer with an extension to break of just a few percent, whereas P4HB is a strong extensible polymer with an extension to break of about 1,000%. Not surprisingly, substantially different conditions are required to process these two polymers, and the resulting products have substantially different properties. The polymers also have substantially different solubilities in organic solvents, and different in vivo degradation rates.

U.S. Pat. Nos. 6,245,537, 6,623,748, 7,244,442, and 8,231,889 describe methods of making PHA polymers and copolymers thereof with little to no endotoxin, which are suitable for medical applications. U.S. Pat. Nos. 6,548,569, 6,838,493, 6,867,247, 7,268,205, 7,179,883, 7,268,205, 7,553,923, 7,618,448 and 7,641,825 and WO 2012/064526 describe use of PHAs to make medical devices. Copolymers of P4HB include 4-hydroxybutyrate copolymerized with 3-hydroxybutyrate or glycolic acid (U.S. Pat. No. 8,039,237 to Martin and Skraly, U.S. Pat. No. 6,316,262 to Huisman et al., and U.S. Pat. No. 6,323,010 to Skraly et al.). Methods to control molecular weight of PHA polymers have been disclosed by U.S. Pat. No. 5,811,272 to Snell et al.

PHAs with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, S. F., et al., *Polyesters, III,* 4:91-127 (2002), Martin, D. et al. Medical Applications of Poly-4-hydroxybutyrate: A Strong Flexible Absorbable Biomaterial, *Biochem. Eng. J.* 16:97-105 (2003), and Williams, S. et al. Poly-4-hydroxybutyrate (P4HB): a new generation of resorbable medical devices for tissue repair and regeneration, *Biomed. Tech.* (Berl) ISSN (Online) 1862-278X, ISSN (Print) 0013-5585, DOI: 10.1515/bmt-2013-0009, 2013. Medical devices and applications of P4HB have also been disclosed by WO 00/56376 to Williams et al. Several patents including U.S. Pat. Nos. 6,555,123, 6,585,994, and 7,025,980 to Williams and Martin describe the use of PHAs in tissue repair and engineering.

WO 2007/092417 to Rizk et al. discloses compositions of PLA (polylactic acid) toughened with P4HB suitable for medical applications.

US Patent Application No. 20050025809 to Hasirci discloses drug uniformly distributed in an un-oriented P4HB homopolymer, at a loading up to 50%, and wherein less than 60% of the drug is released in vitro after 10 days. Hasirci does not disclose oriented fibers or meshes of P4HB, or methods to produce such constructs containing antimicrobial agents with highly oriented P4HB and copolymers thereof.

U.S. Pat. No. 8,034,270 to Martin discloses methods to prepare oriented fibers and meshes of P4HB using melt-extrusion. However, Martin does not disclose methods to prepare oriented P4HB fibers and meshes that contain antimicrobial agents.

U.S. Pat. No. 7,641,825 to Rizk discloses methods to prepare oriented fibers of P4HB by melt extrusion with a decreased tendency to curl. The methods incorporate relaxation and annealing steps to prepare the fibers. Rizk does not disclose methods to prepare oriented fibers of P4HB that contain antimicrobial agents.

U.S. Pat. No. 8,016,883 to Coleman discloses devices made from P4HB multifilament fabrics and non-wovens for tendon and ligament repair. Coleman discloses that an antibiotic may be added to the tendon and ligament devices, but does not disclose specific antibiotics, or methods to add the antibiotics without damaging the P4HB fabrics and non-wovens.

U.S. Pat. No. 7,618,448 to Schmitz discloses absorbable stents made from specific blends of PLA and P4HB, and stent coatings that incorporate P4HB. Schmitz also discloses therapeutic agents that could be incorporated into the PLA/P4HB stent, such as anti-inflammatory agents, immunomodulators, and anti-proliferative agents. Schmitz also discloses that antibiotic agents may be incorporated into PLA/P4HB stents or stent coatings for urological application. However, Schmitz does not disclose (i) the preparation of resorbable P4HB devices (only blends with 70% or more PLA that have substantially different properties to P4HB), or (ii) oriented forms of P4HB containing antimicrobial agents, including oriented fibers and meshes.

U.S. Pat. No. 7,943,683 to Rizk discloses oriented films of P4HB and P4HB copolymers that are produced by solvent casting and melt extrusion. Rizk does not disclose films containing antimicrobial agents.

U.S. Pat. No. 8,287,909 to Martin discloses melt-blown non-wovens of P4HB. Martin does not disclose non-wovens containing antimicrobial agents.

U.S. Pat. No. 8,747,468 to Martin discloses spin finishes that can be applied to fibers of P4HB and copolymers thereof during the manufacture of medical devices, and suture coatings, and collagen sponges reinforced by PHA meshes. The collagen sponges can carry antibiotics. However, Martin does not disclose how to prepare oriented PHA fibers and meshes with antimicrobial agents.

US Patent Application No. 20120150285 to Cahil discloses un-oriented dry spun nonwovens of P4HB, but does not disclose dry spun nonwovens of P4HB and copolymers thereof with antimicrobial agents.

US Patent Application No. 20130309275 to Carter discloses compositions of P4HB and copolymers thereof filled with bioceramics, but does not disclose bioceramic compositions containing antimicrobial agents.

US Patent Application No. 20140200667 to Carter discloses P4HB fibers braided and knitted into structures for osteochondral repair, but does not disclose such structures containing antimicrobial agents.

US Patent Application No. 20130309166 to Rizk discloses processes to injection mold compositions of P4HB, but does not disclose injection molded compositions comprising P4HB and copolymers thereof with antimicrobial agents.

US Patent Application No. 20120283826 to Moses discloses mastopexy implants, which may be made from P4HB. However, Moses does not disclose P4HB fibers or meshes with antimicrobial agents.

Thus, there is no disclosure of oriented fibers and meshes of P4HB and copolymers thereof that contain antimicrobial agents, or methods that would be necessary to form such devices.

B. Additives

Certain additives may be incorporated into P4HB and copolymers thereof prior to converting these compositions into oriented resorbable implants. Preferably, these additives are incorporated during the compounding process to produce pellets that can be subsequently processed into oriented implants. For example, additives may be compounded with P4HB, the compounded P4HB extruded into pellets, and the pellets extruded into oriented fibers suitable for making monofilament meshes. In another embodiment, the additives may be incorporated using a solution-based process. In a preferred embodiment, the additives are biocompatible, and even more preferably the additives are both biocompatible and resorbable.

In one embodiment, the additives may be nucleating agents and/or plasticizers. These additives may be added in sufficient quantity to produce the desired result. In general, these additives may be added in amounts of up to 20% by weight. Nucleating agents may be incorporated to increase the rate of crystallization of the P4HB or copolymer thereof. Such agents may be used, for example, to improve the mechanical properties of fibers and meshes, and to reduce cycle times. Preferred nucleating agents include, but are not limited to, salts of organic acids such as calcium citrate, polymers or oligomers of PHA polymers and copolymers, high melting polymers such as polyglycolic acid ("PGA"), talc, micronized mica, calcium carbonate, ammonium chloride, and aromatic amino acids such as tyrosine and phenylalanine.

Plasticizers that may be incorporated into the compositions include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydofiurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

In another preferred embodiment, the additives are contrast agents, radiopaque markers and radioactive substances. These additives may also be incorporated into P4HB or copolymer thereof either before preparing oriented implants, such as fibers and meshes, or after they are prepared.

C. Therapeutic, Prophylactic, Cosmeceutical, and Diagnostic Agents

1. Antimicrobial Agents

Antimicrobial agents that may be incorporated into the oriented implants of P4HB and copolymers thereof, include, but are not limited to, antibacterial drugs, antiviral agents, antifungal agents, and antiparisitic drugs. Antimicrobial agents include substances that kill or inhibit the growth of microbes such as microbicidal and microbiostatic agents. Antimicrobial agents that may be incorporated into the oriented implants of P4HB and copolymers thereof, include, but are not limited to: rifampin; minocycline and its hydrochloride, sulfate, or phosphate salt; triclosan; chlorhexidine; vancomycin and its hydrochloride, sulfate, or phosphate salt; tetracycline and its hydrochloride, sulfate, or phosphate salt, and derivatives; gentamycin; cephalosporin antimicrobials; aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts, ethylsuccinate, and stearate forms thereof, clindamycin; clindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; clarithromycin; and silver ions, salts, and complexes. In a preferred embodiment the antimicrobial agents incorporated into the implants are (i) rifampin and (ii) minocycline and its hydrochloride, sulfate, or phosphate salt. In a particularly preferred embodiment the oriented implants of P4HB and copolymer thereof comprise rifampin and minocycline or its hydrochloride, sulfate, or phosphate salt.

2. Other Therapeutic, Prophylactic, Cosmeceutical and Diagnostic Agents which can be Incorporated If desired, the oriented implants of P4HB and copolymers thereof may incorporate bioactive agents in addition to antimicrobial agents. These bioactive agents may be added during the formulation process, during pelletization or blending, or may be added later to the oriented implants (including during the addition of the antimicrobial agents).

In a preferred embodiment, the agents improve cell attachment, tissue in-growth, and tissue maturation. The implants can contain active agents designed to stimulate cell in-growth, including growth factors, cellular differentiating factors, cellular recruiting factors, cell receptors, cell-binding factors, cell signaling molecules, such as cytokines, and molecules to promote cell migration, cell division, cell proliferation and extracellular matrix deposition. Such active agents include fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insulin-like growth factor (IGF), hepatocyte growth factor (HGF), interleukin-1-B (IL-1B), interleukin-8 (IL-8), and nerve growth factor (NGF), and combinations thereof.

Other bioactive agents include oncological agents, anti-scarring agents, anti-inflammatory agents, anesthetics, small molecule drugs, anti-angiogenic factors and pro-angiogenic factors, immunomodulatory agents, and blood clotting agents.

The bioactive may be proteins such as collagen and antibodies, peptides, polysaccharides such as chitosan, alginate, polysaccharides such as hyaluronic acid and derivatives thereof or heparin, nucleic acid molecules, small molecular weight compounds such as steroids, inorganic materials such as hydroxyapatite, or complex mixtures such as platelet rich plasma. Suitable antimicrobial agents include: bacitracin, biguanide, trichlosan, gentamicin, minocycline, rifampin, vancomycin, cephalosporins, copper, zinc, silver, and gold. Nucleic acid molecules may include DNA, RNA, siRNA, miRNA, antisense or aptamers.

Diagnostic agents include contrast agents, radiopaque markers, or radioactive substances which may be incorporated into the implants.

The implants may also contain allograft material and xenograft materials.

In yet another embodiment, the implants may incorporate systems for the controlled release of the therapeutic or prophylactic agents.

III. Oriented Implants of P4HB and Copolymers Thereof Containing Antimicrobial Agents and Methods of Manufacturing A. Oriented Implants of P4HB and Copolymers Thereof Antimicrobial agents may be incorporated into any oriented implant of P4HB and copolymers thereof. Oriented implants include, but are not limited to, fibers (including monofilament fibers, multifilament fibers, braids and barbed fibers), meshes (including monofilament and multifilament meshes, and combinations thereof), woven constructs, non-woven constructs, films, patches, tubes, laminates, or pultruded profiles. The implants may be monoaxially oriented or biaxially oriented.

In a preferred embodiment, the oriented implants are P4HB monofilament meshes. The oriented P4HB monofilament fibers used to make these meshes may be prepared by melt extrusion or solution spinning. In a preferred embodiment, the oriented P4HB monofilament fibers are made by melt extrusion, and may be prepared as described by WO 2011/119742 to Martin et al. and U.S. Pat. No. 8,034,270 to Martin et al.

The diameters of the oriented P4HB monofilament fibers may range from 10 µm to 1 mm, but more preferably have a diameter ranging from 50 µm to 600 µm, and even more preferably from 50 µm to 250 µm. The exact mechanical properties of the oriented fibers will depend upon the degree of orientation. In a particularly preferred embodiment, the oriented P4HB monofilament fibers will have one or more of the following properties: a tensile strength of at least 100 MPa, more preferably at least 300 MPa, and even more preferably at least 450 MPa; an elongation to break of less than 500%, more preferably less than 300%, and even more preferably less than 100%; a tensile modulus of at least 100 MPa, more preferably at least 300 MPa, and even more preferably at least 500 MPa. In another embodiment, the oriented P4HB monofilament fibers have a melt temperature of at least 62° C.

In another embodiment, the oriented implants comprise P4HB multifilament fibers. Oriented P4HB multifilament fibers may be prepared by melt extrusion or solution spinning. In a preferred embodiment, the P4HB multifilament fibers are made by melt extrusion, and may be prepared as described by WO 2011/119742 to Martin et al. and U.S. Pat. No. 8,034,270 to Martin et al. In an embodiment the oriented P4HB multifilament fibers are prepared with a denier per filament (dpf) greater than 2. In another embodiment, the multifilament fibers are prepared with a tenacity of greater than 2 gram/denier, and more preferably greater than 4 gram/denier.

B. Methods of Making Oriented Meshes of P4HB and Copolymers Thereof

In a preferred embodiment, the oriented implants comprise P4HB monofilament meshes. Suitable oriented P4HB monofilament meshes may be made as disclosed by WO 2011/119742 to Martin et al. and U.S. Pat. No. 8,034,270 to Martin et al.

In an embodiment, the oriented P4HB meshes have one or more of the following properties: a suture pullout strength of at least 3 kgf; a ball burst strength measured using a ⅜ inch ball of at least 22 lb. force; pore diameters that are at least 50 µm, more preferably at least 100 m, and even more preferably over 250 µm; a Taber stiffness that is less than 100 Taber stiffness units, and more preferably less than 10 Taber stiffness units, and fiber diameters ranging from 10 m to 1 mm.

In a preferred embodiment, the P4HB mesh is made from P4HB monofilament fiber. In a more preferred embodiment, the P4HB monofilament mesh has a knitted or woven structure. A particularly preferred P4HB monofilament mesh has one or more of the following properties: a pore diameter of 500 µm+100 µm, thickness of 0.5 mm±0.2 mm, areal density of approx. 182 g/m²±40 g/m² suture pullout strength of 5.6 kgf±1 kgf, and a burst strength of 24.5 Kg±5 Kg.

In another embodiment, the oriented P4HB meshes may comprise different sized fibers or other non-PHA fibers, including P4HB multifilament, and fibers made from other absorbable or non-absorbable biocompatible polymers.

C. Method of Incorporating Antimicrobial Agents into Oriented Implants of P4HB and Copolymers Thereof Incorporation of antimicrobial agents into oriented implants of P4HB and copolymers is challenging because exposure of these implants to many processing conditions leads to loss of orientation, and therefore an undesirable loss of mechanical properties, including in vivo strength retention. For example, oriented forms of P4HB have relatively low melting points. Exposure of oriented P4HB to temperatures above its melting point during processing leads rapidly to loss of orientation, and loss of mechanical strength. Similarly, exposure of P4HB to antimicrobial solutions containing solvents such as polar organics like methylene chloride, chloroform and tetrahydrofuran will also result in loss of orientation and loss of mechanical strength. These processing constraints are further complicated by the stability of the antimicrobial agents, and processing methods that are compatible with these agents. For example, it may be possible to use a solution of an antimicrobial agent in a polar solvent like chloroform to coat other polymeric oriented implants with the antimicrobial agent, but this approach will cause loss of orientation of the oriented P4HB implants. Antimicrobial agents may also have poor stability in certain solvents. The choice of processing options is also further restricted by biocompatibility constraints, excluding, for example, a further set of solvents from consideration because of their toxicity.

In one embodiment, the oriented implants of P4HB and copolymers thereof may be coated with solutions of antimicrobial agents in non-solvents for P4HB and copolymers thereof. Suitable non-solvents include methanol, ethanol, ethyl acetate, water, and acetonitrile. Preferred non-solvents are water and methanol. The concentration of the antimicrobial agent or agents in the solvent can range from about 0.1 mg/mL to about 100 mg/mL, preferably from about 1 mg/mL to about 30 mg/mL. The amount (density of coverage) of each antimicrobial coated on the orthopedic implant can range from about 1 $\mu g/cm^2$ to about 1000 $\mu g/cm^2$, or preferably, from about 50 $\mu g/cm^2$ to about 200 $\mu g/cm^2$. In various embodiments, the amount ranges from about 10 $\mu g/cm^2$ to about 175 $\mu g/cm^2$, or from about 10 $\mu g/cm^2$ to about 150 $\mu g/cm^2$, or from about 10 $\mu g/cm^2$ to about 100 $\mu g/cm^2$, or from about 10 $\mu g/cm^2$ to about 75 mg/cm$^2$, or from about 20 $\mu g/cm^2$ to about 200 $\mu g/cm^2$ or from about 50 $\mu g/cm^2$ to about 200 $\mu g/cm^2$, or from about 75 $\mu g/cm^2$ to about 200 $\mu g/cm^2$ or from about 100 $\mu g/cm^2$ to about 200 $\mu g/cm^2$, or from about 150 $\mu g/cm^2$ to about 200 $\mu g/cm^2$.

In a preferred embodiment, the oriented implants of P4HB and copolymers thereof, are coated with rifampin and minocycline (including its hydrochloride, sulfate, or phosphate salt). The antimicrobial agents may be applied to the oriented implants individually, or from a solution containing both antimicrobial agents. Rifampin may be applied to the oriented implants of P4HB and copolymers thereof from solutions comprising the following non-solvents: water, ethyl acetate, methanol, ethanol, and acetonitrile. Concentrations of rifampin in ethyl acetate, methanol, ethanol, and acetonitrile may be up to 25 mg/mL. The concentration of rifampin in water may be, for example, up to 1.3 mg/mL at pH 4.3, or 2.5 mg/mL at pH 7.3. Minocycline (including its hydrochloride, sulfate, or phosphate salt) may be applied to oriented implants of P4HB and copolymers thereof from solutions comprising the following non-solvents: water, methanol, and ethanol. Concentrations of minocycline (including its hydrochloride, sulfate, or phosphate salt) in water may be up to 50 mg/mL. In a particularly preferred embodiment, rifampin and minocycline (including its hydrochloride, sulfate, or phosphate salt) may be dissolved in the same solution, and coated on the oriented implants comprising P4HB and copolymers thereof. Preferred solvents for simultaneously coating both rifampin and minocycline (including its hydrochloride, sulfate, or phosphate salt) onto oriented implants of P4HB and copolymers thereof, from a single solution, are water and methanol.

In an even more preferred embodiment, the oriented implants comprising P4HB and copolymers thereof, may be coated with solutions of antimicrobial agents dissolved in poor solvents for P4HB and copolymers thereof. These poor solvents do not cause significant loss of orientation of the implants. However, these poor solvents allow the antimicrobial agents to slightly soften and penetrate the surfaces of the implants. This has two main advantages. First, it allows the implants to be coated with higher concentrations of antimicrobial agents, and second it allows the antimicrobial agents to diffuse into the implants. Diffusion of the antimicrobial agents into the implants results in a more prolonged release profile, and an increased ability of the implant to prevent colonization of the implants, and reduce or prevent the occurrence of infection following implantation in a patient. Suitable poor solvents that can dissolve antimicrobial agents, but not cause loss of orientation of the implants, include aqueous or alcoholic solutions of tetrahydrofuran (THF), dimethylsulfoxide (DMSO), dimethyl formamide (DMF), and dimethyl acetamide (DMA). Alcohols that may be combined with these solvents include methanol and ethanol. The concentration of the antimicrobial agent(s) in the poor solvents can range from about 0.1 mg/mL to about 100 mg/mL, preferably from about 1 mg/mL to about 30 mg/mL. The amount (density of coverage) of each antimicrobial coated on the implant can range from about 1 $\mu g/cm^2$ to about 1000 $\mu g/cm^2$, or preferably, from about 50 $\mu g/cm^2$ to about 200 $\mu g/cm^2$. In various embodiments, the amount ranges from about 10 $\mu g/cm^2$ to about 175 $\mu g/cm^2$, or from about 10 $\mu g/cm^2$ to about 150 $\mu g/cm^2$, or from about 10 $\mu g/cm^2$ to about 100 $\mu g/cm^2$, or from about 10 $\mu g/cm^2$ to about 75 mg/cm$^2$, or from about 20 $\mu g/cm^2$ to about 200 $\mu g/cm^2$ or from about 50 $\mu g/cm^2$ to about 200 $\mu g/cm^2$, or from about 75 $\mu g/cm^2$ to about 200 $\mu g/cm^2$ or from about 100 $\mu g/cm^2$ to about 200 $\mu g/cm^2$, or from about 150 $\mu g/cm^2$ to about 200 $\mu g/cm^2$.

In a preferred embodiment, the oriented implants of P4HB and copolymers thereof, are coated with rifampin and minocycline (including its hydrochloride, sulfate, or phosphate salt) dissolved in poor solvents for P4HB and copolymers thereof. The antimicrobial agents may be applied to the oriented implants individually using the same or different poor solvents, or from a single solution containing both antimicrobial agents in a poor solvent. In one embodiment, rifampin may be applied to the oriented implants of P4HB and copolymers thereof from solutions comprising the following poor solvents (i) THF, (ii) DMSO, (iii) DMF and (iv) DMA each mixed with one or more of the following: water, methanol and/or ethanol. In another embodiment, minocycline may be applied to the oriented implants of P4HB and copolymers thereof from solutions in the following poor solvents: THF/water, THF/methanol, and THF/ethanol. In a preferred embodiment, rifampin and minocycline (including its hydrochloride, sulfate, or phosphate salt forms) are dissolved in a solution of THF/water, THF/ethanol or THF/ethanol, and applied to the oriented implants.

The solutions of the antimicrobial agents in non-solvents or poor solvents can be applied to the oriented implants of P4HB and copolymers thereof in any appropriate manner. For example, coating solutions containing the antimicrobial agents can be brush coated, spray coated, roll coated, printed, sputtered and dip coated. A preferred method for applying the coating solution is spray coating with ultrasonic atomization assisted spraying.

One or more coatings of the antimicrobial coating solutions can be applied to the oriented implants of P4HB and copolymers thereof. In one embodiment, the coating solution is applied in several coats, ranging from 1 to 100, depending upon the amount of antimicrobial agent(s) to be applied to the implant.

The coating solutions described herein may optionally incorporate other components, including polymers and bioactive agents. Other polymers, include, but are not limited to, poly(lactides); poly(glycolides); poly(lactide-co-glycolides); poly(lactic acid); poly(glycolic acid); poly(lactic acid-co-glycolic acids); polycaprolactones; poly(orthoesters); polyanhydrides; poly(phosphazenes); synthetically or biologically prepared polyesters (including polyesters with one or more of the following monomeric units: glycolic, lactic; trimethylene carbonate, p-dioxanone, or ε-caprolactone); poly(lactide-co-caprolactones); polycarbonates; tyrosine polycarbonates; polyamides (including synthetic and natural polyamides, polypeptides, and poly(amino acids)); polyesteramides; poly(dioxanones); poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); chitin; chitosan; modified chitosan; collagen; silk; biocompatible polysaccharides; biocompatible copolymers (including block copolymers or random copolymers); hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide, or polycaprolcatone or combinations thereof. These polymers or bioactive agents may also be applied in a separate step.

The antimicrobial coated oriented implants of P4HB and copolymers thereof may also be top coated with a polymer. One advantage of adding a topcoat is to slow the release of the antimicrobial agents. Suitable polymers that could be applied include polymers soluble in non-solvents for P4HB and copolymers thereof. For example, absorbable biocompatible water soluble polymers, such as cellulose polymers, dextrans, polyethylene glycols, polyethylene oxides, polylysine, poly-maleic acid, polyvinyl acetates, polyvinyl alcohols, poly(oxyethylene) sorbitan monolaurate, silk, hyaluronic acid and derivatives thereof, collagen, and other proteins and polysaccharides. Other polymers that can be used as a topcoat include poly(lactides); poly(glycolides); poly(lactide-co-glycolides); poly(lactic acid); poly(glycolic acid); poly(lactic acid-co-glycolic acids); polycaprolactones; poly(orthoesters); polyanhydrides; poly(phosphazenes); synthetically or biologically prepared polyesters (including polyesters with one or more of the following monomeric units: glycolic, lactic; trimethylene carbonate, p-dioxanone, or ε-caprolactone); poly(lactide-co-caprolactones); polycarbonates; tyrosine polycarbonates; polyamides (including synthetic and natural polyamides, polypeptides, and poly(amino acids)); polyesteramides; poly(dioxanones); poly(alkylene alkylates); polyethers; polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); chitin; chitosan; modified chitosan; biocompatible polysaccharides; biocompatible copolymers (including block copolymers or random copolymers); hydrophilic or water soluble polymers, such as polyethylene glycol, (PEG) or polyvinyl pyrrolidone (PVP) with blocks of other biocompatible or biodegradable polymers, for example, poly(lactide), poly(lactide-co-glycolide, or polycaprolactone or combinations thereof.

After coating of the oriented implants with the antimicrobial agent or agents, the implants may be dried to remove the solvent. Any suitable method may be used to dry the implant, including evaporation at room temperature (20-22° C.) or at elevated temperature. However, the oriented implants should not be heated to a temperature much higher than 60-70° C. so that loss of orientation or melting of the implants is avoided. In one preferred embodiment, the implants may be dried at temperatures up to 55° C. Even more preferably, the implants may be dried at temperatures up to 55° C. in the presence of a vacuum.

In a preferred embodiment, the oriented implants comprising P4HB and copolymers thereof, and one or more antimicrobial agents, release the antimicrobial agent(s) for at least 2 days following implantation.

In another embodiment, the coating methods disclosed herein may be used to coat the following oriented structures of P4HB and copolymers thereof with antimicrobial agent(s): fibers (including monofilament fibers, multifilament fibers, braids and barbed fibers), meshes (including monofilament and multifilament meshes, and combinations thereof), woven constructs, non-woven constructs, films, patches, tubes, laminates, or pultruded profiles. In a particularly preferred embodiment, the coating methods described herein may be used to prepare implants comprising fibers, meshes, and woven constructs made from P4HB and copolymers thereof that contain both rifampin and minocycline. These fibers, meshes and woven implants may be used, for example, in hernia repair, breast reconstruction and augmentation, mastopexy, orthopedic repairs, wound management, pelvic floor reconstruction, stenting, heart valve surgeries, dental procedures and other plastic surgeries.

In a preferred embodiment, the coating methods may be used to form oriented implants comprising P4HB and copolymers thereof that are coated with antimicrobial agents, wherein the implants are: suture, barbed suture, wound closure device, patch, wound healing device, wound dressing, burn dressing, ulcer dressing, skin substitute, hemostat, tracheal reconstruction device, organ salvage device, dural patch or substitute, nerve regeneration or repair device, hernia repair device, hernia mesh, hernia plug, device for temporary wound or tissue support, tissue engineering scaffold, guided tissue repair/regeneration device, anti-adhesion membrane or barrier, tissue separation membrane, retention membrane, sling, device for pelvic floor reconstruction, urethral suspension device, device for treatment of urinary incontinence, bladder repair device, bulking or filling device, bone marrow scaffold, bone plate, fixation device for an implant, ligament repair device or augmentation device, anterior cruciate ligament repair device, tendon repair device or augmentation device, rotator cuff repair device, meniscus repair or regeneration device, articular cartilage repair device, osteochondral repair device, spinal fusion device, cardiovascular patch, catheter balloon, vascular closure device, intracardiac septal defect repair device, including but not limited to atrial septal defect repair devices and PFO (patent foramen ovale) closure devices, left atrial appendage (LAA) closure device, pericardial patch, vein valve, heart valve, vascular graft, myocardial regeneration device, periodontal mesh, guided tissue regeneration membrane for periodontal tissue, ocular cell implant, imaging device, cochlear implant, anastomosis device, cell seeded device, cell encapsulation device, controlled release device, drug delivery device, plastic surgery device, breast lift device, mastopexy device, breast reconstruction device, breast augmentation device (including devices for use with breast implants), breast reduction device (including devices for removal, reshaping and reorienting breast tissue), devices for breast reconstruction following mastectomy with or without breast implants, facial reconstructive device, forehead lift device, brow lift device, eyelid lift device, face lift device, rhytidectomy device, thread lift device (to lift and support sagging areas of the face, brow and neck), rhinoplasty device, device for malar augmentation, otoplasty device, neck lift device, mentoplasty device, cosmetic repair device, and device for facial scar revision.

In another embodiment, the coating methods described herein may be used to prepare resorbable enclosures, pouches, holders, covers, meshes, non-wovens, films, clamshells, casings, and other receptacles made from P4HB and copolymers thereof that can be used to partially or fully encase, surround or hold implantable medical devices, and wherein the P4HB and copolymers thereof contain and release one or more antimicrobial agents to prevent colonization of the implants and/or reduce or prevent infection. Implantable medical devices that can be partially or fully encased include cardiac rhythm management (CRM) devices (including pacemakers, defibrillators, and generators), implantable access systems, neurostimulators, ventricular access devices, infusion pumps, devices for delivery of medication and hydration solutions, intrathecal delivery systems, pain pumps, and other devices to provide drugs or electrical stimulation to a body part. In a preferred embodiment, the resorbable enclosures, pouches, holders, covers, meshes, non-wovens, films, clamshells, casings, and other receptacles made from P4HB and copolymers thereof that partially or fully encase, surround or hold implantable medical devices contain rifampin and minocycline.

The antimicrobial coated oriented implants of P4HB and copolymers thereof can be sterilized by gamma irradiation, electron beam irradiation (e-beam), or exposure to ethylene oxide. They may also be sterilized by rinsing with alcohol such as ethanol. The implants should not however be sterilized by steam sterilization as this will cause the implants to lose orientation, and potentially melt. In a preferred embodiment, implants of P4HB and copolymers thereof that contain rifampin and minocycline are sterilized using cold ethylene oxide.

IV. Methods of Delivery of Oriented Implants of P4HB and Copolymers Thereof Containing Antimicrobial Agents The oriented implants for P4HB and copolymers thereof containing antimicrobial agents may be implanted using traditional open surgery techniques, and may also, if desired, be implanted using minimally invasive techniques.

In a particularly preferred embodiment, the implants comprising oriented fibers, meshes and woven constructs comprising rifampin and minocycline are implanted using minimally invasive techniques when used for hernia repair, breast reconstruction and augmentation, mastopexy, orthopedic repairs, pelvic floor reconstruction, stenting, heart valve surgeries, and other plastic surgeries.

In a preferred embodiment, the antimicrobial containing resorbable enclosures, pouches, holders, covers, meshes, non-wovens, films, clamshells, casings, and other receptacles made from oriented P4HB and copolymers thereof are used to partially or fully encase, surround or hold implantable medical devices prior to implantation. These implantable medical devices include cardiac rhythm management (CRM) devices (including pacemakers, defibrillators, and generators), implantable access systems, neurostimulators, ventricular access devices, infusion pumps, devices for delivery of medication and hydration solutions, intrathecal delivery systems, pain pumps, and other devices to provide drugs or electrical stimulation to a body part.

The present invention will be further understood by reference to the following non-limiting examples.

Example 1: Preparation of P4HB Monofilament by Melt Extrusion

Materials and Methods

Bulk P4HB resin in pellet form was dried to under 300 ppm water using a rotary vane vacuum pump system. The dried resin was transferred to an extruder feed hopper with nitrogen purge to keep the pellets dry. The pellets were gravity fed into a chilled feeder section and introduced into the extruder barrel, which was 1.50 inches in diameter and fitted with an extrusion screw with a 30:1 L/D ratio. The extruder barrel contained 5 heating zones (or extrusion zones)—zones 1, 2, 3, 4 and 5, and was manufactured by American Kuhne. The heated and softened resin from the extruder was fed into a heated metering pump (melt pump) and from the melt pump the extruded resin was fed into the heated block and an eight hole spinneret assembly. Processing profile ranges from 40° C. to 260° C. for temperatures, and 400 psi to 2000 psi for pressures, were used. The molten filaments were water quenched and conveyed into a three-stage orientation, with inline relaxation, before winding of the monofilaments on spools.

Results

Test values for extruded monofilament fiber are shown in Table 2.

TABLE 2

| Mechanical Test Data for P4HB Monofilament Fiber | | | |
| --- | --- | --- | --- |
| Fiber USP Size | Diameter, mm | Breaking Strength, Kg | Break Elongation |
| 5/0 | 0.150 | 1.80 | 30% |
| 6/0 | 0.100 | 1.00 | 29% |

Example 2: Preparation of a P4HB Monofilament Mesh

Spools with P4HB monofilament fiber prepared as described in Example 1 were converted into P4HB monofilament mesh as follows: Monofilament fibers from 49 spools were mounted on a creel, aligned side by side and pulled under uniform tension to the upper surface of a "kiss" roller. The "kiss" roller was spinning while semi-immersed in a bath filled with a 10% solution of TWEEN® 20 lubricant (Polysorbate 20. PEG(20)sorbitan monolaurate. CAS number 9005-64-5). The TWEEN® 20 lubricant was deposited on the surface of the sheet of fiber. Following the application of TWEEN® 20, the sheet of fiber was passed into a comb guide and then wound on a warp beam. A warp is a large wide cylinder onto which individual fibers are wound in parallel to provide a sheet of fibers. Next, warp beams were converted into a finished mesh fabric by means of interlocking knit loops. Eight warp beams were mounted in parallel onto tricot machine let-offs and fed into the knitting elements at a constant rate determined by the 'runner length'. Each individual monofilament fiber from each beam was fed through a series of dynamic tension elements down into the knitting 'guides'. Each fiber was passed through a single guide, which was fixed to a guide bar. The guide bar directed the fibers around the needles forming the mesh fabric structure. The mesh fabric was then pulled off the needles by the take down rollers at a constant rate of speed determined by the fabric 'quality'. The mesh fabric was then taken up and wound onto a roll ready for scoring.

Example 3: Scouring of P4HB Monofilament Mesh and Cytotoxicity Testing

Materials and Methods

The P4HB monofilament mesh produced according to the method of Example 2 was scored ultrasonically with water, heat set in hot water, and then washed with a 70% aqueous ethanol solution. Cytotoxicity testing of two grams of the mesh was undertaken using the ISO Elution Method (1×MEM Extract) following the guidelines of the International Organization for Standardization 10993: Biological Evaluation of Medical Devices, Part 5: Tests for Cytotoxicity: in vitro Methods.

Results

The scoured P4HB monofilament mesh passed the cytotoxicity testing.

The scored P4HB monofilament mesh produced according to Example 3 may be coated with rifampin and minocycline hydrochloride by dissolving these antimicrobial agents in water at concentrations up to 1.3 mg/mL and 50 mg/mL, respectively, and spray coating or dip coating the mesh in the aqueous solution one or more times. If desired, the mesh may be allowed to dry between each coating at room temperature (20-22° C.). Rifampin and minocycline may also be applied to the mesh from a methanol solution where the antimicrobial agents are dissolved at concentrations up to 25 mg/mL. In a third method, rifampin and minocycline hydrochloride are dissolved in water at concentrations up to 1.3 mg/mL and 50 mg/mL, respectively, THF is added, and the mesh is coated with the antimicrobial agents in the water/THF solution.

Modifications and variations of the invention described herein will be obvious to those skilled in the art and are intended to come within the scope of the appended claims.

We claim:

1. An implant comprising an oriented form of P4HB or copolymer thereof and a coating comprising one or more antimicrobial agents, wherein the implant is resorbable, and wherein the oriented form has one or more of the following properties: tensile strength greater than 126 MPa, and a tensile modulus greater than 100 MPa.

2. The implant of claim 1, wherein the implant has been coated with a solution comprising one or more antimicrobial agents.

3. The implant of claim 1, wherein the one or more antimicrobial agents has diffused into the oriented form of P4HB or copolymer thereof.

4. The implant of claim 2, wherein the solution is a poor solvent for the oriented form of P4HB or copolymer thereof.

5. The implant of claim 4, wherein the poor solvent includes one or more of the following: water, alcohol, methanol, ethanol, ethyl acetate, and acetonitrile.

6. The implant of claim 5, wherein the poor solvent is an alcoholic or aqueous solution.

7. The implant of claim 6, wherein the alcoholic or aqueous solution further comprises THF, dimethylsulfoxide, dimethyl formamide and dimethyl acetamide.

8. The implant of claim 1, wherein the oriented form is a monofilament mesh with one or more of the following properties: suture pullout strength of at least 3 kgf, or ball burst strength measured using a ⅜ inch ball of at least 22 lbf.

9. The implants of claim 1, wherein the oriented form comprises oriented fibers and one or more antimicrobial agents, and wherein the oriented fibers are coated with the one or more antimicrobial agents without substantial loss of strength.

10. The implant of claim 1, wherein the implant comprises a resorbable enclosure, pouch, holder, cover, fiber, monofilament fiber, multifilament fiber, braid, barbed fiber, mesh, non-woven, film, tube, woven mesh, knitted mesh, monofilament mesh, multifilament mesh, laminate, pultruded profile, clamshell, casing, or other receptacle designed to partially or fully encase, surround or hold an implantable medical device.

11. The implant of claim 1, wherein the one or more antimicrobial agents are selected from one or more of the following: rifampin; minocycline; minocycline hydrochloride; minocycline sulfate; minocycline phosphate salt; triclosan; chlorhexidine; vancomycin; vancomycin hydrochloride; vancomycin sulfate; vancomycin phosphate salt; tetracycline; tetracycline hydrochloride; tetracycline sulfate; tetracycline phosphate salt; tetracycline derivatives; gentamycin; cephalosporin antimicrobials; aztreonam; cefotetan; cefotetan disodium salt; loracarbef; cefoxitin; cefoxitin sodium salt; cefazolin; cefazolin sodium salt; cefaclor; ceftibuten; ceftibuten sodium salt; ceftizoxime; ceftizoxime sodium salt; cefoperazone; cefoperazone sodium salt; cefuroxime; cefuroxime sodium salt; cefuroxime axetil; cefprozil; ceftazidime; cefotaxime; cefotaxime sodium salt; cefadroxil; ceftazidime; ceftazidime sodium salt; cephalexin; cefamandole nafate; cefepime; cefuroxime hydrochloride; cefuroxime sulfate; cefuroxime phosphate salt; cefdinir; cefdinir sodium salt; ceftriaxone; ceftriaxone sodium salt; cefixime; cefixim sodium salt; cefpodoxime proxetil; meropenem; meropenem sodium salt; imipenem; imipenem sodium salt; cilastatin; cilastatin sodium salt; azithromycin; clarithromycin; dirithromycin; erythromycin; erythromycin hydrochloride; erythromycin sulfate; erythromycin phosphate salt; ethylsuccinate; stearate forms of ethylsuccinate; clindamycin; clindamycin hydrochloride; clindamycin sulfate; clindamycin phosphate salt; lincomycin; lincomycin hydrochloride; lincomycin sulfate; lincomycin phosphate salt; tobramycin; tobramycin hydrochloride; tobramycin sulfate; tobramycin phosphate salt; streptomycin; streptomycin hydrochloride; streptomycin sulfate; streptomycin phosphate salt; neomycin; neomycin hydrochloride; neomycin sulfate; neomycin phosphate salt; acetyl sulfisoxazole; colistimethate; colistimethate sodium salt; quinupristin; dalfopristin; amoxicillin; ampicillin; ampicillin sodium salt; clavulanic acid; sodium salt of clavulanic acid; potassium salt of clavulanic acid; penicillin G; penicillin G benzathine; penicillin G procaine salt; penicillin G sodium; penicillin G potassium salt; carbenicillin; carbenicillin disodium; carbenicillin indanyl disodium salt; piperacillin; piperacillisodium salt; ticarcillin; ticarcillin disodium salt; sulbactam; sulbactam sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline; demeclocycline hydrochloride; demeclocycline sulfate; demeclocycline phosphate salt; doxycycline; doxycycline hydrochloride; doxycycline sulfate; doxycycline phosphate salt; oxytetracycline; oxytetracycline hydrochloride; oxytetracycline sulfate; oxytetracycline phosphate salt; chlortetracycline; chlortetracycline hydrochloride; chlortetracycline sulfate; chlortetracycline phosphate salt; metronidazole; dapsone; atovaquone; rifabutin; linezolide; polymyxin B; polymyxin B hydrochloride; polymyxin B sulfate; polymyxin B phosphate salt; sulfacetamide; ulfacetamide sodium salt; clarithromycin; silver ions, silver salts, and silver complexes.

12. The implant of claim 1, wherein the implant is selected from the group: suture, barbed suture, wound closure device, patch, wound healing device, wound dressing, burn dressing, ulcer dressing, skin substitute, hemostat, tracheal reconstruction device, organ salvage device, dural patch or substitute, nerve regeneration or repair device, hernia repair device, hernia mesh, hernia plug, device for temporary wound or tissue support, tissue engineering scaffold, guided tissue repair/regeneration device, anti-adhesion membrane or barrier, tissue separation membrane, retention membrane, sling, device for pelvic floor reconstruction, urethral suspension device, device for treatment of urinary incontinence, bladder repair device, bulking or filling device, bone marrow scaffold, bone plate, fixation device for an implant, ligament repair device or augmentation device, anterior cruciate ligament repair device, tendon repair device or augmentation device, rotator cuff repair device, meniscus repair or regeneration device, articular cartilage repair device, osteochondral repair device, spinal fusion device, cardiovascular patch, catheter balloon, vascular closure device, intracardiac septal defect repair device, atrial septal defect repair devices, patent foramen ovale closure devices, left atrial appendage closure device, pericardial patch, vein valve, heart valve, vascular graft, myocardial regeneration device, periodontal mesh, guided tissue regeneration membrane for periodontal tissue, ocular cell implant, imaging device, cochlear implant, anastomosis device, cell seeded device, cell encapsulation device, controlled release device, drug delivery device, plastic surgery device, breast lift device, mastopexy device, breast reconstruction device, breast augmentation device, breast reduction device, devices for breast reconstruction following mastectomy with or without breast implants, facial reconstructive device, forehead lift device, brow lift device, eyelid lift device, face lift device, rhytidectomy device, thread lift device, rhinoplasty device, device for malar augmentation, otoplasty device, neck lift device, mentoplasty device, cosmetic repair device, and device for facial scar revision.

13. The implant of claim 1, further comprising one or more of the following: plasticizer, nucleant, dye, medical marker, therapeutic agent, diagnostic agent, prophylactic agent, protein, peptide, polysaccharide, glycoprotein, lipid, lipoprotein, nucleic acid molecule, inorganic or organic synthetic molecule, contrast agent, radiopaque marker, radioactive substance, hyaluronic acid or derivative thereof, collagen, hydroxyapatite, or absorbable polymer comprising one or more the following monomeric units: glycolic acid, lactic acid, trimethylene carbonate, p-dioxanone, and caprolactone.

14. The implant of claim 1, wherein the one or more antibiotics are released from the implant for at least 2 days.

15. The implant of claim 1, wherein the implant is used for soft or hard tissue repair, regeneration or replacement.

16. The implant of claim 8, wherein the oriented form comprises oriented fibers and one or more antimicrobial agents, and wherein the oriented fibers are coated with the one or more antimicrobial agents without substantial loss of strength.

\* \* \* \* \*